US008962207B2

(12) United States Patent
Kajiwara et al.

(10) Patent No.: US 8,962,207 B2
(45) Date of Patent: Feb. 24, 2015

(54) GAS DETECTION SYSTEM, VEHICLE, AND CHECKUP METHOD FOR GAS DETECTION SYSTEM (75) Inventors: Shigeto Kajiwara, Okazaki (JP); Katsuki Ishigaki, Handa (JP)

(73) Assignee: Toyota Jidosha Kabushiki Kaisha, Toyota-Shi (JP)

( * ) Notice: Subject to any disclaimer, the term of this patent is extended or adjusted under 35 U.S.C. 154(b) by 406 days.

(21) Appl. No.: 12/681,813

(22) PCT Filed: Oct. 2, 2008

(86) PCT No.: PCT/JP2008/068316
§ 371 (c)(1),
(2), (4) Date: Apr. 6, 2010

(87) PCT Pub. No.: WO2009/048085
PCT Pub. Date: Apr. 16, 2009

(65) Prior Publication Data
US 2010/0233562 A1    Sep. 16, 2010

(30) Foreign Application Priority Data

Oct. 10, 2007   (JP) ................... 2007-263965

(51) Int. Cl.
*H01M 8/04* (2006.01)
*G01N 33/00* (2006.01)
*G01M 3/00* (2006.01)
*G01M 3/22* (2006.01)

(52) U.S. Cl.
CPC .......... *G01N 33/0063* (2013.01); *G01M 3/007* (2013.01); *G01M 3/226* (2013.01)

USPC ................... 429/444; 429/443; 429/449

(58) Field of Classification Search
USPC ......................... 429/443, 444, 449
See application file for complete search history.

(56) References Cited

U.S. PATENT DOCUMENTS

| | | | | |
|---|---|---|---|---|
| 4,390,869 A | * | 6/1983 | Christen et al. | 340/632 |
| 7,242,309 B2 | * | 7/2007 | Yokosawa et al. | 340/632 |
| 2005/0106438 A1 | * | 5/2005 | Hobmeyr | 429/32 |
| 2005/0155405 A1 | * | 7/2005 | Sasaki et al. | 73/1.06 |
| 2005/0228596 A1 | * | 10/2005 | Shoji | 702/24 |

FOREIGN PATENT DOCUMENTS

| | | |
|---|---|---|
| JP | 2001-293476 A | 10/2001 |
| JP | 2004-93204 A | 3/2004 |
| JP | 2006-145252 A | 6/2006 |
| JP | 2006-329786 A | 12/2006 |

* cited by examiner

*Primary Examiner* — Jane Rhee
(74) *Attorney, Agent, or Firm* — Kenyon & Kenyon LLP (57) ABSTRACT A gas detection system functions to detect a specific gas present in a certain space. The gas detection system includes a gas concentration detector arranged to detect concentration of the specific gas as a gas concentration. The gas detection system also has a determination module configured to determine whether the gas concentration detected by the gas concentration detector exceeds a set threshold value. In response to input of a checking instruction for checking up the gas concentration detector into the determination module, the determination module uses a threshold value for checkup purpose, in place of the set threshold value. This arrangement effectively enhances the convenience in the process of checking up the gas concentration detector.

9 Claims, 5 Drawing Sheets

GAS DETECTION SYSTEM, VEHICLE, AND CHECKUP METHOD FOR GAS DETECTION SYSTEM

This is a 371 national phase application of PCT/JP2008/068316 filed 2 Oct. 2008, which claims priority of Japanese Patent Application No. 2007-263965 filed 10 Oct. 2007, the contents of which are incorporated herein by reference.

TECHNICAL FIELD

The present invention relates to a gas detection technology.

BACKGROUND ART

In a vehicle equipped with a fuel cell system, a hydrogen detector is generally provided to detect the occurrence of a leakage of hydrogen supplied as a fuel gas for fuel cells. An ECU (electronic control unit), for example, determines whether a hydrogen concentration detected by the hydrogen detector exceeds a preset threshold value. In response to the detected hydrogen concentration exceeding the preset threshold value, an alarm lamp may be lit to inform the user of the occurrence of a hydrogen leakage. One proposed technique sprays a test gas onto the hydrogen detector provided in the vehicle to check the condition of the hydrogen detector (see, for example, Japanese Patent Laid-Open No. 2006-329786 and No. 2004-93204).

The test gas sprayed onto the hydrogen detector to check the condition of the hydrogen detector typically has a higher concentration than the preset threshold value. Lighting of the alarm lamp informs the user of the normal functionality of the hydrogen detector.

In the case where multiple hydrogen detectors are installed in the vehicle, the respective hydrogen detectors may have different threshold values as criterion for determining the normal functionality or the abnormality. For example, one hydrogen detector may be installed in a fuel cell casing for storage of fuel cells, while another hydrogen detector may be installed in proximity to a hydrogen tank. The fuel cell casing has a limited space and accordingly has a high potential for ignition even at a significantly low concentration of hydrogen. A relatively small value should thus be set to the threshold value for the hydrogen detector installed in the fuel cell casing. The hydrogen detector installed in the proximity to the hydrogen tank is close to the hydrogen tank and thus naturally tends to detect a high hydrogen concentration. A relatively large value should thus be set to the threshold value for the hydrogen detector installed near to the hydrogen tank. In this manner, multiple different threshold values should be set according to the installation locations of the respective hydrogen detectors by taking into account the size of the space and the distance from a location with a potential hydrogen leakage.

In order to check the conditions of the multiple hydrogen detectors, multiple test gases having different gas concentrations should be provided according to the installation locations of the respective hydrogen detectors. This undesirably makes the checkup of the hydrogen detectors rather complicated. The test gas used for the checkup purpose typically has a fixed gas concentration. Providing the multiple test gases having different gas concentrations corresponding to the multiple different threshold values, however, undesirably consumes both the time and the cost.

This problem is not characteristic of the hydrogen detectors installed in the vehicle but may be commonly found in hydrogen detectors installed in any of various other locations, for example, inside a garage or inside a building. This problem is also not characteristic of the hydrogen detectors but may be commonly found in other gas detectors configured to detect various gases, for example, gasoline, methanol, carbon monoxide, and propane gas.

SUMMARY

In order to solve such a problem of the prior art technique discussed above, there would be a requirement for enhancing the convenience in the process of checking up gas detectors.

One aspect of the invention provides a gas detection system configured to detect a specific gas present in a certain space, the gas detection system comprising:

a gas concentration detector arranged to detect concentration of the specific gas as a gas concentration; and a determination module configured to determine whether the gas concentration detected by the gas concentration detector exceeds a set threshold value, wherein in response to input of a checking instruction for checking up the gas concentration detector into the determination module, the determination module uses a threshold value for checkup purpose, in place of the set threshold value.

In response to input of a checking instruction for checking up the gas concentration detector, the gas detection system according to this aspect of the invention uses the threshold value for the checkup purpose, in place of the set threshold value that is generally used for detection of a gas leakage. When a general-purpose test gas is not usable to check up the gas concentration detector, for example, when the set threshold value is greater than the concentration of the general-purpose test gas, setting a smaller value than the concentration of the general-purpose test gas to the threshold value for the checkup purpose enables the general-purpose test gas to be used for checking up the gas concentration detector. This arrangement desirably reduces both the time and the cost for custom-ordered preparation of the test gas corresponding to the set threshold value, thus enhancing the convenience in the process of checking up the gas concentration detector.

The gas detection system may have multiple gas concentration detectors, wherein the determination module determines whether the gas concentration detected by each of the multiple gas concentration detectors exceeds a threshold value individually set corresponding to the each of the multiple gas concentration detectors, and in response to input of a checking instruction for checking up the respective gas concentration detectors into the determination module, the determination module uses a common threshold value commonly set for the multiple gas concentration detectors, as the threshold value for the checkup purpose to be used in place of the set threshold value.

In the gas detection system of this embodiment, only one test gas having an identical concentration is sufficient to check up the multiple gas concentration detectors, which may have multiple different threshold values set corresponding thereto. This arrangement effectively enhances the convenience in the process of checking up the multiple gas concentration detectors.

The gas detection system may further include:

an informing unit configured to inform a user of a predetermined piece of information, based on a result of the determination by the determination module.

In one application of the gas detection system mounted on a vehicle, the informing unit may inform a driver of the vehicle of the occurrence of a gas leakage. At the checkup time, on the other hand, the same informing unit is used to inform a checker to a checkup result.

In the specification hereof, the terminology 'user' may represent any of various users of the gas detection system or a checker of the gas concentration detector. In one application of the gas detection system mounted on a vehicle, the user of the gas detection system may be, for example, a driver of the vehicle. In another application of the gas detection system installed in a garage, the user of the gas detection system may be, for example, an owner of the garage or a user of the garage.

The gas detection system may further include:

a first informing unit configured to inform a user of a predetermined piece of information, based on a result of the determination with the set threshold value by the determination module; and a second informing unit configured to inform the user of another predetermined piece of information, based on a result of the determination with the threshold value for the checkup purpose by the determination module.

In one application of the gas detection system mounted on a vehicle, for example, the first informing unit may be an alarm device provided in the vehicle, while the second informing unit may be a checking tool. These two informing units inform the user of the results of the determinations.

The gas detection system wherein the threshold value for the checkup purpose may be set to be smaller than the set threshold value.

This arrangement enables a low-concentration gas to be used as the test gas.

The technique of the present invention may be actualized by diversity of applications including a gas detection system, a vehicle equipped with the gas detection system, and a gas detection method.

BEST MODES OF CARRYING OUT THE INVENTION

Figure 1:
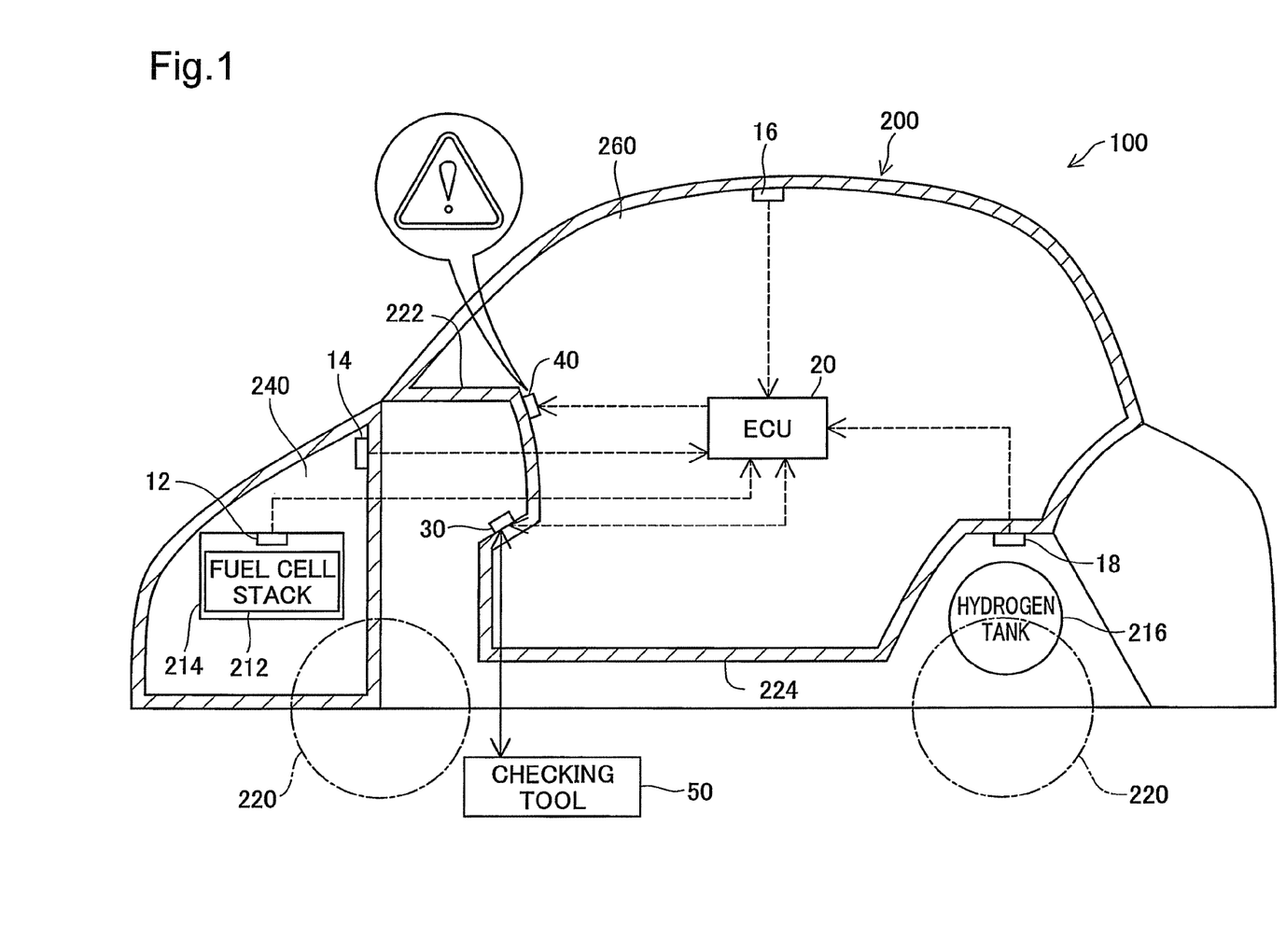
FIG. 1 is an explanatory view illustrating the schematic configuration of a hydrogen detection system 100 in a first embodiment according to the invention.

Some modes of carrying out the invention are described below in the following sequence with reference to the accompanied drawings:
A. First Embodiment
B. Second Embodiment
C. Third Embodiment
D. Other Aspects
A. First Embodiment FIG. 1 is an explanatory view illustrating the schematic configuration of a hydrogen detection system 100 in a first embodiment according to the invention. In this embodiment, the hydrogen detection system 100 is mounted on a fuel cell vehicle 200 equipped with a fuel cell system.

The hydrogen detection system 100 of this embodiment functions to detect a leakage of hydrogen from a fuel cell stack 212 or from a hydrogen tank 216, based on a detection value (hydrogen concentration) sent from any of hydrogen sensors installed in the fuel cell vehicle 200 and inform a driver or a checker of the occurrence of a hydrogen leakage. When the detection value of a hydrogen sensor exceeds a preset threshold value (first threshold value V1) individually set according to the installation position of the hydrogen sensor, an alarm lamp 40 is lit to inform the driver of the occurrence of a hydrogen leakage. At the checkup time of each of the hydrogen sensors, the hydrogen detection system 100 uses a second threshold value V2 for checking, in place of the first threshold value V1 individually set for detection of a hydrogen leakage, and determines whether the detection value of each hydrogen sensor exceeds the second threshold value V2. The configuration and the operations of the hydrogen detection system 100 will be discussed later in detail.

A1. Configuration of Fuel Cell Vehicle

The fuel cell vehicle 200 mainly includes the fuel cell system, the hydrogen detection system 100, a secondary battery (not shown), a motor (not shown), and a PCU (power control unit) (not shown). The fuel cell vehicle 200 activates the motor with the power supplied from the fuel cell stack 212 and the secondary battery as power sources and is driven with the driving power of the motor. Specifically, the fuel cell stack 212 functions as a main power source, while the secondary battery functions as an auxiliary power source. The PCU controls the power supply from the fuel cell stack 212 and the secondary battery to the motor. A rotation shaft of the motor is coupled with wheels 220 via a shaft and other relevant components (not shown). The motor is driven to give driving power to the fuel cell vehicle 200. FIG. 1 shows only the structure relevant to the scope of the invention in the configuration of the fuel cell vehicle 200, and the other structure is omitted from the illustration.

The fuel cell system mainly includes the fuel cell stack 212, a hydrogen supply system arranged to supply hydrogen as a fuel gas, an air supply system arranged to supply the air as an oxidizing gas, and a cooling water circulation system arranged to cool down the fuel cell stack 212. In this embodiment, the fuel cell stack 212 represents a stack of polymer electrolyte fuel cells provided in a fuel cell casing 214. As shown in FIG. 1, the fuel cell stack 212 is installed in an engine compartment 240, a space where an engine is to be installed in a conventional engine vehicle, located in a front portion of the fuel cell vehicle 200. The engine compartment 240 is defined by a hatched frame line in FIG. 1. In the hydrogen supply system, hydrogen is supplied from the hydrogen tank 216 as a storage vessel of high-pressure hydrogen to anodes of the individual fuel cells. In the air supply system, the air compressed by a compressor (not shown) is supplied to cathodes of the individual fuel cells. As shown in FIG. 1, the hydrogen tank 216 is placed under a floor panel 224 in the vicinity of rear wheels.

A2. Configuration of Hydrogen Detection System

The hydrogen detection system 100 mainly includes hydrogen sensors 12, 14, 16, and 18, an ECU 20, input/output terminals 30, and the alarm lamp 40. As shown in FIG. 1, the hydrogen sensor 12, the hydrogen sensor 14, the hydrogen sensor 16, and the hydrogen sensor 18 are respectively installed in the fuel cell casing 214, in the engine compartment 240, in a passenger compartment 260, and in proximity to the hydrogen tank 216. The passenger compartment 260 is defined by a hatched frame line in FIG. 1. Although the ECU 20 is actually placed inside an instrument panel 222, for the clarity of illustration, the ECU 20 is shown in the middle of the passenger compartment 260 in FIG. 1.

Each of the hydrogen sensors 12, 14, 16, and 18 detects the hydrogen concentration and sends the result of the detection to the ECU 20. The ECU 20 is constructed as a microcomputer-based logic circuit to perform various controls (discussed later) related to the operations of the hydrogen detection system 100. The input/output terminals 30 are placed inside the instrument panel 222 and are arranged to be connectable with a checking tool 50. Signals are transmitted between the ECU 20 and the checking tool 50 via the input/output terminals 30. The checking tool 50 may be, for example, a fault diagnosis device used for checkup and servicing in automobile dealers. In the structure of this embodiment, the checking tool 50 has a display unit 52 to display the checking result (diagnosis code) of each hydrogen sensor. The alarm lamp 40 is provided on the instrument panel 222 and is lit in response to an instruction from the ECU 20.

The ECU 20, the input/output terminals 30, and the alarm lamp 40 may be designed exclusively for the hydrogen detection system 100 or may alternatively be designed to have additional functions. For example, the PCU controlling the fuel cell system as mentioned above may be constructed to have the functions of the ECU 20. In another example, the input/output terminals 30 may be designed to be connectable with another tool, for example, a checking tool for checking up the secondary battery or a checking tool for checking up the fuel cell stack 212. The alarm lamp 40 may be designed to be lit in response to detection of any of various faults or abnormalities, for example, a fault detected in the secondary battery or a fault detected in the fuel cell stack 212, as well as in response to detection of a hydrogen leakage.

The hydrogen sensors 12, 14, 16, and 18 in this embodiment are respectively equivalent to the gas concentration detectors in the claims of the invention. The alarm lamp 40 and the checking tool 50 in this embodiment respectively correspond to the first informing unit and the second informing unit in the claims of the invention.

Figure 2:
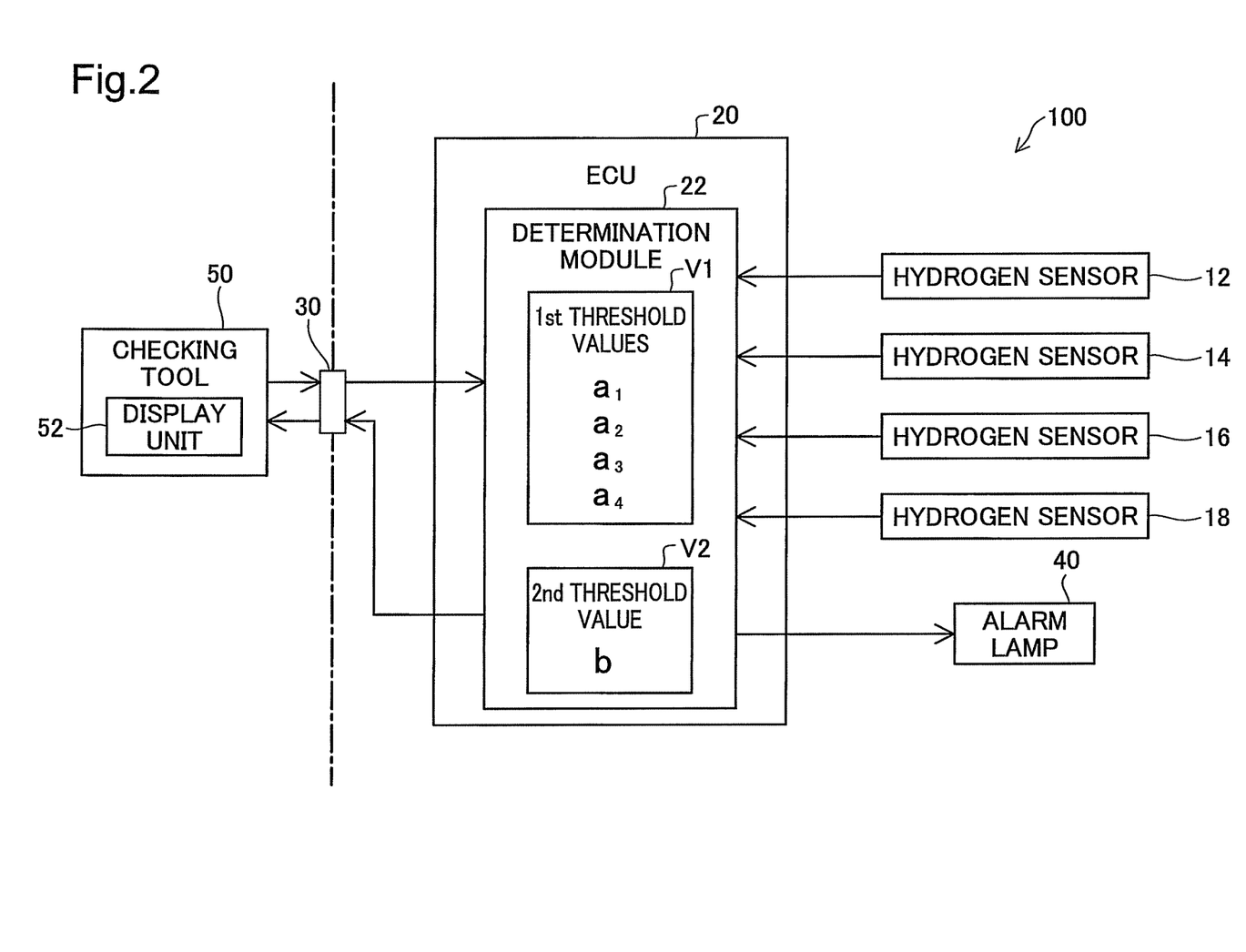
FIG. 2 is a block diagram showing the functions of an ECU 20.

FIG. 2 is a block diagram showing the functions of the ECU 20. As illustrated, the ECU 20 includes a determination module 22 as a functional module. The determination module 22 stores therein four values a1, a2, a3, and a4 set as the first threshold values V1 and one value b set as the second threshold value V2. The determination module 22 detects a hydrogen leakage, based on one of the first threshold values V1. In response to the presence of a checking instruction to check up the respective hydrogen sensors, the determination module 22 uses the second threshold value V2 and determines whether each of the hydrogen sensors is normal or abnormal, that is, whether each of the hydrogen sensors has normal functionality or has any abnormality or fault. Specifically the determination module 22 uses the value a1 as the first threshold value to detect a hydrogen leakage, based on the detection value of the hydrogen sensor 12, while using the value a2 as the first threshold value to detect a hydrogen leakage, based on the detection value of the hydrogen sensor 14. Similarly the determination module 22 uses the value a3 for the hydrogen sensor 16, while using the value a4 for the hydrogen sensor 18. At the checkup time, the determination module 22 uses the value b as the second threshold value V2 for all the hydrogen sensors 12 through 18 and determines whether each of the hydrogen sensors 12 through 18 has normal functionality or has any abnormality or fault.

The four values set as the first threshold values V1 satisfy a magnitude relation of a1<a2<a3<a4. The value b set as the second threshold value V2 is smaller than the smallest first threshold value a1. Namely the value b set as the second threshold value V2 is smaller than all the four values set as the first threshold values V1.

Connection of the checking tool 50 with the input/output terminals 30 causes the determination module 22 to identify the presence of a checking instruction. Upon such identification, the determination module 22 uses the second threshold value V2, in place of each of the first threshold values V1 individually set for the corresponding hydrogen sensors 12 through 18, and determines whether the detection value (hydrogen concentration) of each hydrogen sensor exceeds the second threshold value V2.

In the course of the determination with one of the first threshold values V1 to detect a hydrogen leakage, the determination module 22 outputs an instruction to light the alarm lamp 40, based on the detection value of the hydrogen sensor exceeding the first threshold value V1. In the course of determination with the second threshold value V2 to check up each of the hydrogen sensors, on the other hand, the determination module 22 outputs a diagnosis code representing the normal condition of the hydrogen sensor to the checking tool 50, based on the detection value of the hydrogen sensor exceeding the second threshold value V2.

A3. Operations of Hydrogen Detection System

Figure 3:
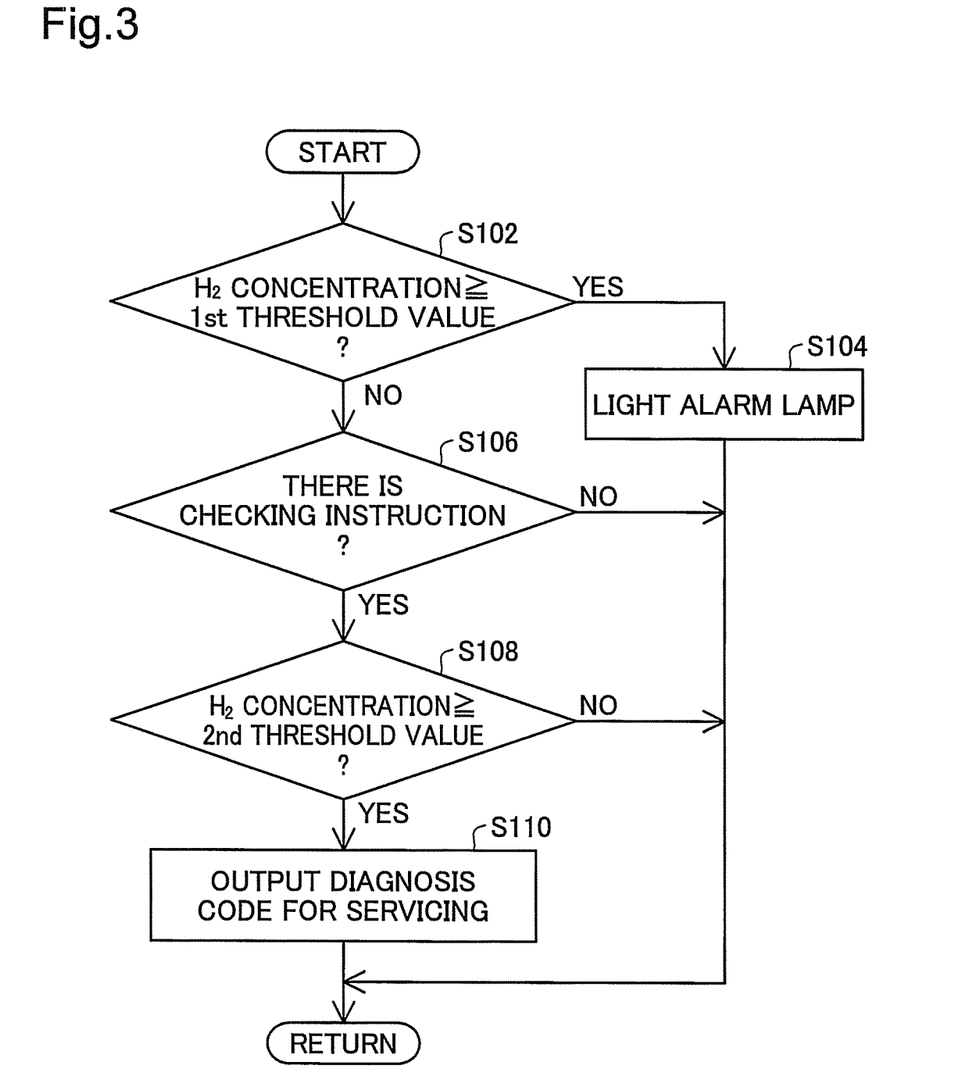
FIG. 3 is a flowchart showing a hydrogen detection system control routine executed by the ECU 20.

FIG. 3 is a flowchart showing a hydrogen detection system control routine executed by the ECU 20. The hydrogen detection system control routine is performed repeatedly at preset time intervals. The processing flow performs the hydrogen detection system control routine with sequentially changing the object to be processed from the hydrogen sensor 12 to the hydrogen sensor 18. A set of these cycles of the hydrogen detection system control routine is defined as one execution unit, which is repeated at the preset time intervals.

In this embodiment, at the checkup time of each of the hydrogen sensors, a checker connects the checking tool 50 with the input/output terminals 30 via a connection cable, powers on the checking tool 50 in the state of power supply to the hydrogen detection system 100 triggered by an ON operation of an ignition switch (not shown) of the fuel cell vehicle 200, and sequentially sprays a test hydrogen gas, which is used for the checkup purpose, onto each of the hydrogen sensors 12 through 18. The checker may be a service representative who is in charge of checking and servicing in an automobile dealer or may be a general user. When the checking tool 50 is connected with the input/output terminals 30 via the connection cable and is powered on, the determination module 22 identifies the presence of a checking instruction.

The ordinary hydrogen leakage detection process performed in the state of no connection of the checking tool 50 with the input/output terminals 30 is explained first with reference to the flowchart of FIG. 3. The determination module 22 first determines whether the hydrogen concentration detected by the hydrogen sensor 12 is greater than the value a1 set as the corresponding first threshold value V1 (step S102). Upon determination that the detected hydrogen concentration is less than the first threshold value V1 (step S102: No), the determination module 22 subsequently identifies the presence or the absence of a checking instruction from the checking tool 50 (step S106).

As mentioned above, since the checking tool 50 is not connected with the input/output terminals 30 at this moment, the determination module 22 identifies the absence of a checking instruction (step S106: No) and returns the routine to step S102. In the next cycle of this routine, the determination module 22 uses the value a2 as the first threshold value V1 to determine whether the detection value (hydrogen concentration) of the hydrogen sensor 14 is greater than the first threshold value a2 at step S102. Similarly the determination module 22 uses the value a3 as the first threshold value V1 to determine whether the detection value of the hydrogen sensor 16 is greater than the first threshold value a3, and uses the value a4 as the first threshold value V1 to determine whether the detection value of the hydrogen sensor 18 is greater than the first threshold value a4. When a certain time period has elapsed since completion of the determinations based on the respective detection values of all the hydrogen sensors 12 through 18, the hydrogen detection system control routine is activated again to start the determination based on the detection value of the hydrogen sensor 12. Namely the hydrogen detection system control routine is repeatedly performed during the power supply to the hydrogen detection system 100. In the structure of this embodiment, the power supply to the hydrogen detection system 100 is triggered by an ON operation of the ignition switch (not shown) of the fuel cell vehicle 200.

In the course of the repeated execution of the hydrogen detection system control routine, upon determination at step S102 that the hydrogen concentration detected by one of the hydrogen sensors 12 through 18 exceeds the corresponding first threshold value V1, the determination module 22 sends an alarm lamp lighting instruction to the alarm lamp 40 to light the alarm lamp 40 (step S104). The lighting of the alarm lamp 40 informs the checker of the occurrence of a hydrogen leakage. In addition to such lighting information, a stop command may be sent to stop the running fuel cell vehicle 200.

The hydrogen sensor checkup process performed in the state of connection of the checking tool 50 with the input/output terminals 30 is described below. In this embodiment, the hydrogen concentration of the test hydrogen gas used for the checkup purpose is set to be less than all the first threshold values V1 (a1, a2, a3, and a4). It is assumed here that no hydrogen leakage occurs in the fuel cell vehicle 200.

The checker first sprays the test hydrogen gas onto the hydrogen sensor 12 to check the condition of the hydrogen sensor 12. The determination module 22 determines whether the hydrogen concentration detected by the hydrogen sensor 12 is greater than the value a1 set as the corresponding first threshold value V1 (step S102). Since the hydrogen concentration of the test hydrogen gas is less than the first threshold value V1 (the value a1), it is determined that the detection value (hydrogen concentration) of the hydrogen sensor 12 is less than the first threshold value V1 (step S102: No).

The determination module 22 subsequently identifies the presence or the absence of a checking instruction (step S106). Since the checking tool 50 has been connected with the input/output terminals 30 and powered on, the determination module 22 identifies the presence of a checking instruction (step S106: Yes) and subsequently determines whether the detection value (hydrogen concentration) of the hydrogen sensor 12 is greater than the second threshold value V2 (the value b) (step S108). Since the hydrogen concentration of the test hydrogen gas is greater than the second threshold value V2, the determination module 22 determines that the detection value is greater than the second threshold value V2 (step S108: Yes) and outputs a diagnosis code for servicing with regard to the hydrogen sensor 12 to the checking tool 50 (step S110). The checking tool 50 receives the diagnosis code for servicing and displays the received diagnosis code for servicing on the display unit 52.

The diagnosis code for servicing with regard to the hydrogen sensor 12 displayed on the display unit 52 of the checking tool 50 informs the checker of the normal functionality of the hydrogen sensor 12.

The determination module 22 performs the determinations with regard to the other hydrogen sensors 14, 16, and 18 in the similar manner to the determination with regard to the hydrogen sensor 12 explained above. The test hydrogen gas has not been, however, sprayed onto any of the other hydrogen sensors 14, 16, and 18, so that the diagnosis code for servicing with regard to any of the other hydrogen sensors 14, 16, and 18 is not displayed on the display unit 52 of the checking tool 50.

The checker subsequently sprays the test hydrogen gas onto the hydrogen sensor 14 to check the condition of the hydrogen sensor 14. As mentioned above, the hydrogen detection system control routine is performed repeatedly. After the checker sprays the test hydrogen gas onto the hydrogen sensor 14, the determination module 22 determines whether the detection value of the hydrogen sensor 14 is greater than the second threshold value V2 (step S108). Upon determination that the detection value of the hydrogen sensor 14 exceeds the second threshold value V2 (step S108: Yes), the determination module 22 outputs a diagnosis code for servicing with regard to the hydrogen sensor 14 to the checking tool 50 (step S110). In the event of a fault or an abnormality arising in the hydrogen sensor 14, on the other hand, it is determined that the detection value of the hydrogen sensor 14 is less than the second threshold value V2 (step S108: No). In this case, the determination module 22 does not output the diagnosis code for servicing with regard to the hydrogen sensor 14 to the checking tool 50 but returns the routine to step S102 to perform the determination based on the detection value of the hydrogen sensor 16.

In this manner, the checker sequentially sprays the test hydrogen gas onto the respective hydrogen sensors. The display of the diagnosis code with regard to a hydrogen sensor on the display unit 52 of the checking tool 50 informs the checker of the normal functionality of the hydrogen sensor. Non-display of the diagnosis code with regard to a hydrogen sensor, on the other hand, informs the checker of the presence of some fault or abnormality in the hydrogen sensor.

In the presence of a checking instruction, the determination module 22 performs the determination by comparison between the detection value of each hydrogen sensor and the second threshold value V2. After the checker sequentially sprays the test hydrogen gas onto the respective hydrogen sensors to check the conditions of the hydrogen sensors, the diagnosis codes with regard to the hydrogen sensors having the detection values of greater than the second threshold value V2 are displayed on the display unit 52 of the checking tool 50. For example, when only the hydrogen sensor 14 has a fault and all the other hydrogen sensors 12, 16, and 18 have normal functionalities, the diagnosis codes with regard to the hydrogen sensors 12, 16, and 18 are displayed. The checker is informed of the presence of a fault in the hydrogen sensor 14, based on the display of the diagnosis codes on the display unit 52.

A4. Effects of Embodiment

As described above, in the hydrogen detection system 100 of the embodiment, in the presence of a checking instruction output in response to connection of the checking tool 50 with the input/output terminals 30, the determination module 22 performs the determination by comparison between the detection value of each of the hydrogen sensors and the second threshold value V2, which is used in place of each corresponding first threshold value V1. In a hydrogen detection system including multiple hydrogen sensors as in the embodiment, while different values are set to the first threshold values V1 for the individual hydrogen sensors to detect a hydrogen leakage, one common value is set to the second threshold value V2 to check the conditions of the respective hydrogen sensors. Namely only one test hydrogen gas having an identical hydrogen concentration is sufficient to check the conditions of the respective hydrogen sensors. There is accordingly no need of providing four test hydrogen gases having different hydrogen concentrations corresponding to the different values a1 through a4 set as the first threshold values V1 of the respective hydrogen sensors. This desirably reduces the cost required for checking up the multiple hydrogen sensors and saves the trouble in checking up the respective hydrogen sensors.

B. Second Embodiment

Figure 4:
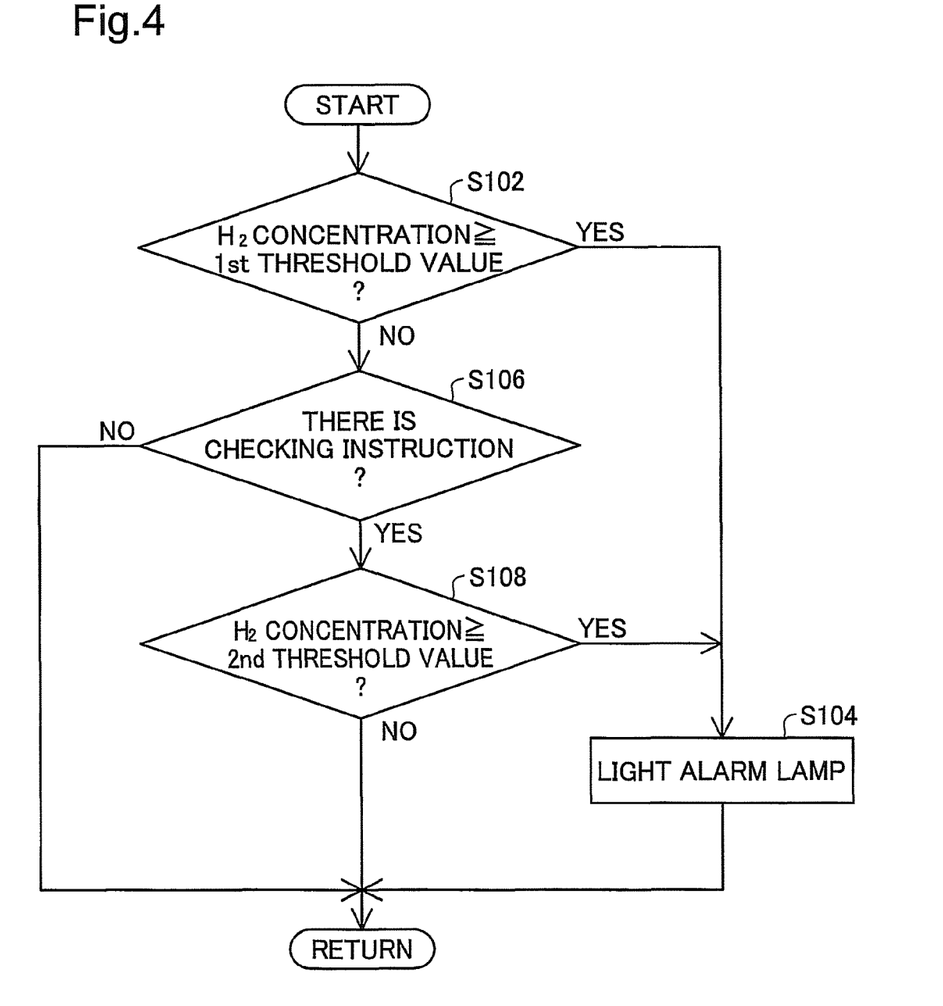
FIG. 4 is a flowchart showing a hydrogen detection system control routine executed by the ECU 20 in a hydrogen detection system of a second embodiment.

FIG. 4 is a flowchart showing a hydrogen detection system control routine executed by the ECU 20 in a hydrogen detection system of a second embodiment. The hydrogen detection system of the second embodiment has substantially the same structure as that of the hydrogen detection system 100 of the first embodiment discussed above, with a difference from the hydrogen detection system control routine executed by the ECU 20 in the hydrogen detection system 100 of the first embodiment. The structure of the hydrogen detection system of the second embodiment is thus not specifically explained here, but only the operations of the hydrogen detection system of the second embodiment are described below with reference to the flowchart of FIG. 4. The second threshold value V2 used in the second embodiment is identical with the second threshold value V2 (the value b) used in the first embodiment.

B1. Operations of Embodiment

The ordinary hydrogen leakage detection process of this embodiment performed in the state of no connection of the checking tool 50 with the input/output terminals 30 is identical with that of the first embodiment and is thus not specifically described here. At the start of the hydrogen sensor checkup process performed in the state of connection of the checking tool 50 with the input/output terminals 30, the checker sprays the test hydrogen gas onto the hydrogen sensor 12 to check the condition of the hydrogen sensor 12. The determination module 22 determines whether the hydrogen concentration detected by the hydrogen sensor 12 is greater than the value a1 set as the corresponding first threshold value V1 (step S102). Since the hydrogen concentration of the test hydrogen gas is less than the value a1, it is determined that the detection value (hydrogen concentration) of the hydrogen sensor 12 is less than the first threshold value V1 (step S102: No).

The determination module 22 subsequently identifies the presence or the absence of a checking instruction (step S106). Since the checking tool 50 has been connected with the input/output terminals 30 and powered on, the determination module 22 identifies the presence of a checking instruction (step S106: Yes) and subsequently determines whether the detection value (hydrogen concentration) of the hydrogen sensor 12 is greater than the second threshold value V2 (step S108). Since the hydrogen concentration of the test hydrogen gas is greater than the value b set as the second threshold value V2, the determination module 22 determines that the detection value is greater than the second threshold value V2 (step S108: Yes) and sends an alarm lamp lighting instruction to the alarm lamp 40 to light the alarm lamp 40 (step S104).

Unlike the first embodiment, the procedure of the second embodiment lights the alarm lamp 40 based on the detection value of a hydrogen sensor exceeding the second threshold value V2 at the checkup time of the hydrogen sensor. The lighting of the alarm lamp 40 informs the checker of the normal functionality of the hydrogen sensor 12. Before checking the condition of the hydrogen sensor 14, the checker should turn off the alarm lamp 40. The checker then sprays the test hydrogen gas onto the hydrogen sensor 14 to check the condition of the hydrogen sensor 14. The alarm lamp 40 in this embodiment is equivalent to the informing unit in the claims of the invention.

B2. Effects of Embodiment

As described above, in the hydrogen detection system of the second embodiment, at the checkup time of the respective hydrogen sensors 12 through 18, the checker is informed of a fault or an abnormality arising in any of the hydrogen sensors 12 through 18, based on lighting or non-lighting of the alarm lamp 40. The technique of the second embodiment is specifically suitable for checking the conditions of hydrogen sensors with a checking tool of the simpler structure without the display unit 52.

C. Third Embodiment

Figure 5:
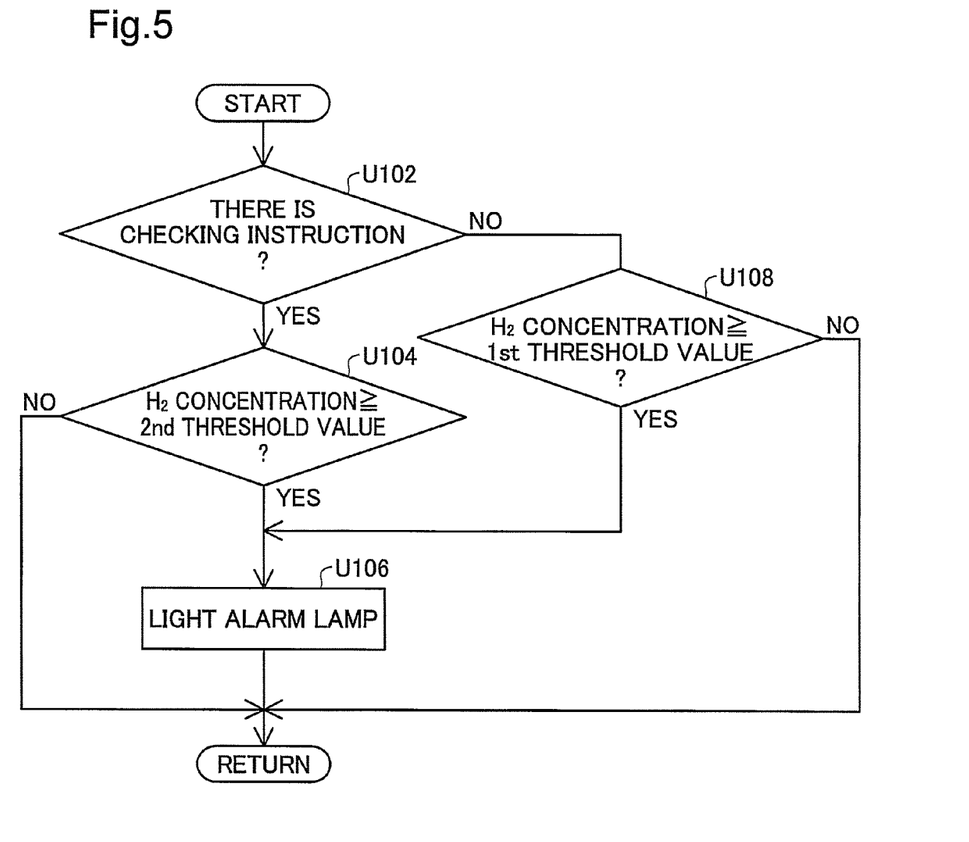
FIG. 5 is a flowchart showing a hydrogen detection system control routine executed by the ECU 20 in a hydrogen detection system of a third embodiment.

FIG. 5 is a flowchart showing a hydrogen detection system control routine executed by the ECU 20 in a hydrogen detection system of a third embodiment. The hydrogen detection system of the third embodiment has substantially the same structure as that of the hydrogen detection system 100 of the first embodiment discussed above, with a difference from the hydrogen detection system control routine executed by the ECU 20 in the hydrogen detection system 100 of the first embodiment. The structure of the hydrogen detection system of the third embodiment is thus not specifically explained here, but only the operations of the hydrogen detection system of the third embodiment are described below with reference to the flowchart of FIG. 5.

C1. Operations of Embodiment

The ordinary hydrogen leakage detection process performed in the state of no connection of the checking tool 50 with the input/output terminals 30 is explained first. The determination module 22 first identifies the presence or the absence of a checking instruction (step U102). Since the checking tool 50 is not connected with the input/output terminals 30 at this moment, the determination module 22 identifies the absence of a checking instruction (step U102: No) and determines whether the detection value of the hydrogen sensor 12 is greater than the value a1 set as the corresponding first threshold value V1 (step U108). When it is determined that the detection value is less than the first threshold value V1 (step U108: No), the determination module 22 returns the routine to step U102 and detects the occurrence of a hydrogen leakage with the values a2, a3, and a4 individually set as the first threshold values V1 for the other hydrogen sensors 14, 16, and 18 (step U108).

Like the procedure of the first embodiment, when a certain time period has elapsed since completion of the determinations based on the respective detection values of all the hydrogen sensors 12 through 18, the hydrogen detection system control routine is activated again to start the determination based on the detection value of the hydrogen sensor 12. Namely the hydrogen detection system control routine is repeatedly performed during the power supply to the hydrogen detection system. As in the first embodiment, when it is determined at step U108 that the hydrogen concentration is greater than the first threshold value V1, the determination module 22 sends an alarm lamp lighting instruction to the alarm lamp 40 to light the alarm lamp 40 (step U106).

The hydrogen sensor checkup process performed in the state of connection of the checking tool 50 with the input/output terminals 30 is described below. At the start of the checkup process, the checker sprays the test hydrogen gas onto the hydrogen sensor 12 to check the condition of the hydrogen sensor 12. The determination module 22 first identifies the presence or the absence of a checking instruction (step U102). Since the checking tool 50 has been connected with the input/output terminals 30 and powered on, the determination module 22 identifies the presence of a checking instruction (step U102: Yes) and subsequently determines whether the detection value (hydrogen concentration) of the hydrogen sensor 12 is greater than the second threshold value V2 (the value b) (step U104). Since the hydrogen concentration of the test hydrogen gas is greater than the value b, the determination module 22 determines that the detection value is greater than the second threshold value V2 (step U104: Yes). The determination module 22 then sends an alarm lamp lighting instruction to the alarm lamp 40 to light the alarm lamp 40 (step U106).

Unlike the first embodiment, in the procedure of the third embodiment, the determination module 22 first identifies the presence or the absence of a checking instruction. In the absence of a checking instruction, the detection value of a hydrogen sensor is compared with the first threshold value V1. In the presence of a checking instruction, on the contrary, the detection value of a hydrogen sensor is compared with the second threshold value V2. As in the procedure of the second embodiment, at the checkup time of a hydrogen sensor, the alarm lamp 40 is lit when the detection value of the hydrogen sensor is greater than the second threshold value V2. The lighting of the alarm lamp 40 informs the checker of the normal functionality of the hydrogen sensor 12.

C2. Effects of Embodiment

The hydrogen detection system of the third embodiment has the similar effects to those of the first embodiment and the second embodiment discussed above. Additionally the procedure of the embodiment first identifies the presence or the absence of a checking instruction. The second threshold value V2 may thus be set to be greater than the first threshold value V1, as well as to be less than the first threshold value V1. Namely the second threshold value V2 may be set arbitrarily according to the concentration of a commercially available test hydrogen gas used for the checkup purpose.

D. Other Aspects

The embodiments and their applications discussed above are to be considered in all aspects as illustrative and not restrictive. There may be many modifications, changes, and alterations without departing from the scope or spirit of the main characteristics of the present invention. Some examples of possible modification are given below.

(1) In the embodiment discussed above, the hydrogen detection system 100 has the four hydrogen sensors. The number and the installation locations of hydrogen sensors are, however, not restricted to those in the structure of the embodiment. Application of a threshold value set for the checkup purpose provides the similar effects to those of the embodiments discussed above, irrespective of the number and the installation locations of the hydrogen sensors.

(2) The hydrogen detection system 100 is mounted on the fuel cell vehicle 200 in the embodiment discussed above. The hydrogen detection system may be installed in any of various spaces, for example, inside a garage for parking a fuel cell vehicle therein or a space with a machine for producing hydrogen gas installed therein.

(3) The above embodiment describes the hydrogen detection system including the hydrogen sensors used for detecting the hydrogen concentration. The technique of the invention is generally applicable to a gas concentration detector used for detecting concentration of any of various other gases, such as gasoline, methanol, carbon monoxide, or propane gas. In any gas detection system for detecting any of these gases, application of a threshold value set for the checkup purpose provides the similar effects to those of the embodiments discussed above.

(4) The procedure of the embodiment lights the alarm lamp when the detection value (hydrogen concentration) of a hydrogen sensor exceeds the first threshold value V1 to inform the user or the checker of the occurrence of a hydrogen leakage. The informing method is, however, not restricted to the alarm lamp. Another informing technique may give a warning message like 'Warning! Hydrogen is Leaked' on a display of the fuel cell vehicle 20. Still another information technique may give an audio warning. Any of these techniques may be combined for the informing purpose.

(5) In the configuration of the embodiment, when the checking tool 50 is connected to the input-output terminals 30 and is powered on, the determination module 22 identifies the presence of a checking instruction. This is, however, not restrictive, and the presence of a checking instruction may be identified on other occasions. One modified procedure may identify the presence of a checking instruction when a checkup command is input from the checking tool 50 via the input-output terminals 30. Another modification may use a checkup button provided to output a checkup command. In response to the checker's operation of the checkup button, the determination module 22 may identify the presence of a checking instruction. At the checkup time of hydrogen sensors, any of these modified procedures uses a threshold value set for the checkup purpose (second threshold value), in place of a threshold value set for the ordinary hydrogen leakage (first threshold value), to be compared with the detection value of a hydrogen sensor, thus providing the similar effects to those of the embodiments discussed above.

The invention claimed is:

1. A gas detection system configured to detect a specific gas present in a certain space, the gas detection system comprising:
    multiple gas concentration detectors installed in at least two of the following different locations: fuel cell casing, an engine compartment, passenger compartment, and proximate to a hydrogen tank, each being arranged to detect specific gas concentrations; and
    a determination module programmed to determine whether the gas concentration detected by each of the multiple gas concentration detectors exceeds a threshold value individually set corresponding to the each of the multiple gas concentration detectors,
    wherein the threshold values set for the multiple gas concentration detectors to be compared with the detected gas concentrations are different from each other,
    wherein in response to input of a checking instruction for checking up the respective gas concentration detectors into the determination module, the determination module is programmed to use a threshold value for checkup purpose, in place of each of the set threshold values, and is programmed to determine whether each of the multiple gas concentration detectors has normal functionality or any abnormality, based on a concentration of a specific gas-containing test gas detected by the gas concentration detector, and
    wherein the threshold value for checkup purpose is set as a common threshold value for all the multiple gas concentration detectors and is a different value from the threshold values set for the multiple gas concentration detectors to be compared with the detected gas concentrations.

2. The gas detection system in accordance with claim 1, the gas detection system further including:

an informing unit configured to inform a user of a predetermined piece of information, based on a result of the determination by the determination module.

3. The gas detection system in accordance with claim 1, the gas detection system further including:
a first informing unit configured to inform a user of a predetermined piece of information, based on a result of the determination with each of the set threshold values by the determination module; and
a second informing unit configured to inform the user of another predetermined piece of information, based on a result of the determination with the threshold value for the checkup purpose by the determination module.

4. The gas detection system in accordance with claim 1, wherein the threshold value for checkup purpose is set to be smaller than a smallest value among the threshold values individually set corresponding to the multiple gas concentration detectors.

5. The gas detection system in accordance with claim 1, wherein the specific gas is hydrogen gas.

6. A vehicle equipped with a fuel cell system and the gas detection system in accordance with claim 5.

7. A checkup method for a gas detection system,
the gas detection system including: multiple gas concentration detectors installed in at least two of the following different locations: fuel cell casing, an engine compartment, passenger compartment, and proximate to a hydrogen tank, each being arranged to detect concentration of a specific gas present in a certain space as a gas concentration; and a determination module configured to determine whether the gas concentration detected by each of the gas concentration detectors exceeds a threshold value individually set corresponding to the each of the multiple gas concentration detectors,
wherein the threshold values set for the multiple gas concentration detectors to be compared with the detected gas concentrations are different from each other,
the checkup method for the gas detection system comprising:
(a) causing the determination module to identify presence or absence of a checking instruction for checking the respective gas concentration detectors; and
(b) upon identification of the presence of the checking instruction by the determination module, causing the determination module to use a threshold value for checkup purpose in place of each of the set threshold values, the threshold value for checkup purpose being set as a common threshold value for all the multiple gas concentration detectors, and determine whether each of the multiple gas concentration detectors has normal functionality or any abnormality, based on a concentration of a specific gas-containing test gas detected by the gas concentration detector and is a different value from the threshold values set for the multiple gas concentration detectors to be compared with the detected gas concentrations.

8. The vehicle in accordance with claim 6, wherein the fuel cell system includes:
fuel cells; and
a hydrogen storage vessel constructed to store hydrogen, which is to be supplied to the fuel cells,
in the gas detection system, the multiple gas concentration detectors including at least one gas concentration detector installed in proximity to the fuel cells and at least one gas concentration detector installed in proximity to the hydrogen storage vessel,
the determination module using the threshold values individually set corresponding to the multiple gas concentration detectors and detecting the occurrence of a hydrogen leakage from the fuel cells and the occurrence of a hydrogen leakage from the hydrogen storage vessel.

9. The checkup method in accordance with claim 7, wherein the threshold value for checkup purpose is set to be smaller than a smallest value among the threshold values individually set corresponding to the multiple gas concentration detectors.

* * * * *